(12) United States Patent
Ogawa et al.

(10) Patent No.: US 9,801,746 B2
(45) Date of Patent: Oct. 31, 2017

(54) STENT INDWELLING DEVICE

(71) Applicant: OLYMPUS CORPORATION, Tokyo (JP)

(72) Inventors: Chieko Ogawa, Tokyo (JP); Yutaka Yanuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 152 days.

(21) Appl. No.: 14/793,912

(22) Filed: Jul. 8, 2015

(65) Prior Publication Data

US 2015/0306346 A1    Oct. 29, 2015

Related U.S. Application Data

(63) Continuation of application No. PCT/JP2014/059606, filed on Apr. 1, 2014.

(30) Foreign Application Priority Data

Jun. 10, 2013   (JP) ................. 2013-122063

(51) Int. Cl.
*A61F 2/06* (2013.01)
*A61F 2/962* (2013.01)
(Continued)

(52) U.S. Cl.
CPC .............. *A61F 2/962* (2013.01); *A61F 2/966* (2013.01); *A61M 25/005* (2013.01);
(Continued)

(58) Field of Classification Search
CPC .......... A61M 25/0043; A61M 25/0045; A61M 25/005; A61M 25/0054;
(Continued)

(56) References Cited

U.S. PATENT DOCUMENTS 5,368,566 A    11/1994  Crocker
5,807,355 A *  9/1998  Ramzipoor ......... A61M 25/104
                                                   604/526
(Continued)

FOREIGN PATENT DOCUMENTS

EP    2489334 A1    8/2012
JP    S63-20854 U   2/1988
(Continued)

OTHER PUBLICATIONS

Extended Supplementary European Search Report dated Dec. 7, 2016 in related European Patent Application No. 14 81 1114.9.
(Continued)

*Primary Examiner* — Richard Louis
(74) *Attorney, Agent, or Firm* — Scully, Scott, Murphy & Presser, P.C.

(57) ABSTRACT

A stent indwelling device includes a guide catheter and a pusher catheter. The guide catheter includes: a core section; an outer layer section surrounding an outer circumference of the core section; a stent protection section disposed between the core section and the outer layer section, being longer than a dimension of a tube stent, having stiffness resisting compression inward in a radial direction perpendicular to a longitudinal axis of the guide catheter, and having flexibility in a direction in which the guide catheter is curved; and a stopper configured to allow expansion of the stent protection section in a direction along the longitudinal axis and restrict movement of the stent protection section in the direction with respect to the core section.

5 Claims, 3 Drawing Sheets

(51) Int. Cl.
*A61F 2/966* (2013.01)
*A61M 25/00* (2006.01)

(52) U.S. Cl.
CPC .... *A61M 25/0043* (2013.01); *A61M 25/0045* (2013.01); *A61M 25/0054* (2013.01); *A61F 2210/0004* (2013.01); *A61F 2240/00* (2013.01); *A61M 2025/0018* (2013.01); *A61M 2025/0059* (2013.01)

(58) Field of Classification Search
CPC ... A61M 2025/0059; A61M 2025/0018; A61F 2/962; A61F 2/966; A61F 2240/00; A61F 2210/0004
See application file for complete search history.

(56) References Cited

U.S. PATENT DOCUMENTS

| | | | |
|---|---|---|---|
| 8,114,144 B2 | 2/2012 | Chow et al. | |
| 2002/0156459 A1* | 10/2002 | Ye | A61L 29/085 604/527 |
| 2005/0049574 A1* | 3/2005 | Petrick | A61M 25/0026 604/525 |
| 2005/0061771 A1* | 3/2005 | Murphy | A61M 25/0012 216/17 |
| 2006/0030835 A1* | 2/2006 | Sherman | A61F 2/958 604/526 |
| 2006/0265047 A1* | 11/2006 | Dorn | A61F 2/95 623/1.12 |
| 2006/0276873 A1* | 12/2006 | Sato | A61B 17/3468 623/1.11 |
| 2008/0051761 A1* | 2/2008 | Slazas | A61M 25/1006 604/527 |
| 2008/0243222 A1* | 10/2008 | Schafersman | A61M 25/0662 623/1.11 |
| 2009/0143849 A1 | 6/2009 | Ozawa et al. | |

FOREIGN PATENT DOCUMENTS

| | | |
|---|---|---|
| JP | 2723672 B2 | 3/1998 |
| JP | 2009-136676 A | 6/2009 |
| JP | 2010-136895 A | 6/2010 |
| JP | 2010-536430 A | 12/2010 |
| WO | 2004/098462 A1 | 11/2004 |
| WO | 2007/095031 A2 | 8/2007 |
| WO | WO 2009/023720 A1 | 2/2009 |
| WO | 2011/091362 A1 | 7/2011 |
| WO | WO 2011/118081 A1 | 9/2011 |
| WO | 2012/068389 A1 | 5/2012 |

OTHER PUBLICATIONS

International Search Report dated Jun. 10, 2014 issued in PCT/JP2014/059606.

* cited by examiner

STENT INDWELLING DEVICE

This application is a continuation application based on PCT Patent Application No. PCT/JP2014/059606, filed Apr. 1, 2014, whose priority is claimed on Japanese Patent Application No. 2013-122063, filed Jun. 10, 2013. The contents of both the PCT Patent Application and the Japanese Patent Application are incorporated herein by reference.

BACKGROUND OF THE INVENTION

Field of the Invention

The present invention relates to a stent indwelling device.

Description of Related Art

In the related art, a tube stent placed in a lumen tissue such as a bile duct, a blood vessel, or the like, is known (for example, see Japanese Unexamined Utility Model Application, First Publication No. S63-20854). In addition, a procedure of releasing stenosis by inserting a tube stent or a metallic stent into a narrowed portion of the bile duct, and performing drainage of bile is known. When an indwelling period of the tube stent is lengthened, a lumen of the tube stent may close and prevent the drainage. As one cause of the lumen of the tube stent closing, an end surface of the tube stent comes in contact with a bile duct wall, and an opening of the tube stent may be closed by the bile duct wall. A phenomenon in which the opening of the tube stent is closed by the bile duct wall is likely to occur in a relatively hard tube stent.

A tube stent provided to reduce the probability that the opening of the tube stent is closed by the bile duct wall is known. The tube stent can be placed along a shape of the lumen tissue because a structure or a material is devised to provide flexibility. In Japanese Unexamined Patent Application, First Publication No. 2010-136895, a thin and soft tube provided to improve kink resistance and tensile strength is disclosed. The tube has a coil layer formed of an element wire constituted by a flat wire, and an outer layer having flexibility and arranged outside the coil layer. An outer surface of the coil layer and an inner surface of the outer layer are fixed to come in contact with each other in a slidable state. In addition, a stent indwelling device provided to place a flexible tube stent is known.

SUMMARY OF THE INVENTION

According to a first aspect of the present invention, a stent indwelling device configured to place a tube stent in a lumen tissue includes: a guide catheter having a longitudinal axis and configured to be inserted into the tube stent from a distal end side of the guide catheter; and a pusher catheter having a lumen into which the guide catheter is inserted. The guide catheter includes: a core section having flexibility and being longer than a dimension in an axial direction of the tube stent; an outer layer section having a tube shape surrounding an outer circumference of the core section and being fixed to the core section; a stent protection section disposed between the core section and the outer layer section, being longer than the dimension in the axial direction of the tube stent, being formed in an annular shape about the longitudinal axis when seen from a direction along the longitudinal axis, having stiffness resisting compression inward in a radial direction perpendicular to the longitudinal axis, and having flexibility in a direction in which the guide catheter is curved; and a stopper configured to allow expansion of the stent protection section in the direction along the longitudinal axis and restrict movement of the stent protection section in the direction along the longitudinal axis with respect to the core section.

According to a second aspect of the present invention, in the stent indwelling device according to the first aspect of the present invention, the core section and the outer layer section may be fixed to each other at a distal end of the outer layer section. A distal end side of the outer layer section may be formed to have a diameter gradually reduced from a proximal end side of the guide catheter toward the distal end side of the guide catheter, and smoothly connected to an outer surface of the core section.

According to a third aspect of the present invention, in the stent indwelling device according to the first aspect of the present invention, the stopper may have a protrusion formed on at least one of the core section and the outer layer section and protruding toward a space between the core section and the outer layer section. The protrusion may be configured to restrict the movement of the stent protection section in the direction along the longitudinal axis by coming in contact with the stent protection section.

According to a fourth aspect of the present invention, in the stent indwelling device according to the first aspect of the present invention, the stent protection section may be constituted by an element wire having a spiral structure of tight winding.

According to a fifth aspect of the present invention, in the stent indwelling device according to the first aspect of the present invention, the outer layer section may be formed in a cylindrical shape having a circular cross-section. The stent protection section may be formed in a substantially cylindrical shape having a circular cross-section. A difference between an inner diameter of the outer layer section and an outer diameter of the stent protection section may be equal to or less than 0.5 mm.

DETAILED DESCRIPTION OF THE INVENTION

Figure 1:
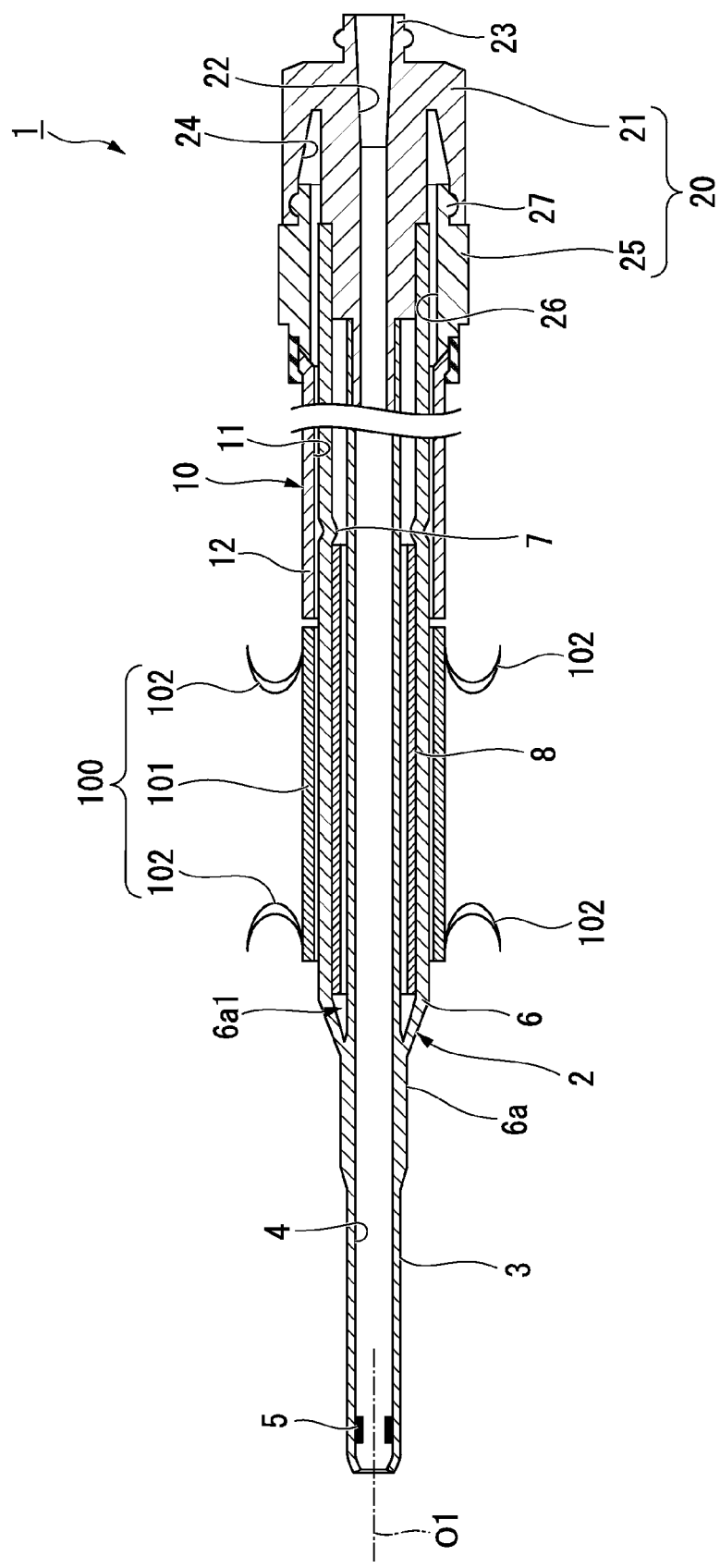
FIG. 1 is a cross-sectional view showing a stent indwelling device according to an embodiment of the present invention.
Figure 2:
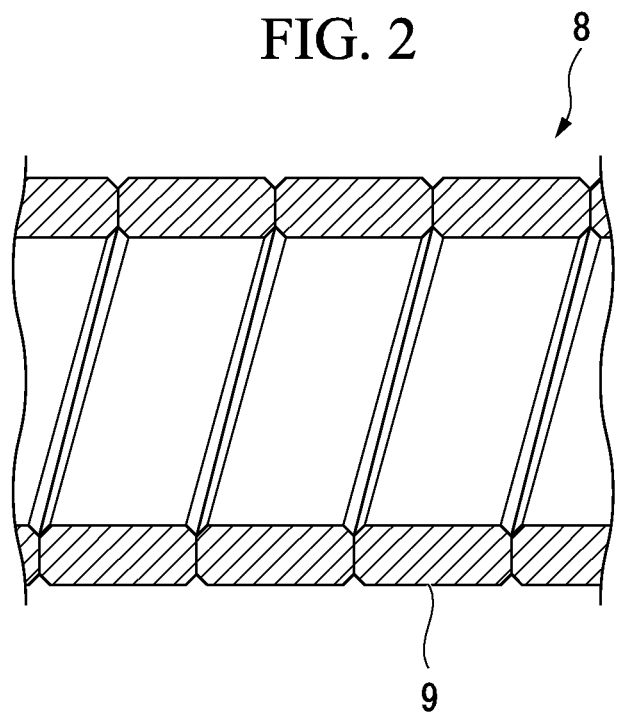
FIG. 2 is a cross-sectional view showing a stent protection section of the stent indwelling device.

A stent indwelling device 1 according to an embodiment of the present invention will be described. FIG. 1 is a cross-sectional view showing the stent indwelling device according to the embodiment. FIG. 2 is a cross-sectional view showing a stent protection section of the stent indwelling device.

As shown in FIG. 1, the stent indwelling device 1 includes a guide catheter 2, a pusher catheter 10, and a hand manipulation part 20. A tube stent 100 is used with the stent indwelling device 1 according to the embodiment. The tube stent 100 is a known stent formed in a cylindrical shape such that a distal end section of the guide catheter 2 can be inserted into the stent. For example, the tube stent 100 has a main body 101 and flaps 102. The main body 101 has flexibility and is formed in a cylindrical shape. The flaps 102 have flexibility and extend from an outer surface of the main body 101 toward the outside in a radial direction of the main body 101. The main body 101 of the tube stent 100 may have a coil configured to hold a cross-section of the lumen of the tube stent 100 in a circular shape.

The guide catheter 2 is a long member having a longitudinal axis O1 and formed in a flexible cylindrical shape on the whole. The guide catheter 2 has a core section 3, an outer layer section 6, a stent protection section 8, and a stopper.

The core section 3 is a flexible elongated member formed of, for example, a resin. In the embodiment, the core section 3 has a cylindrical shape in which a guide wire lumen 4 extending form a proximal end to a distal end of the core section 3 is formed. A guide wire can be inserted through the guide wire lumen 4 of the core section 3 from the distal end of the guide catheter 2 to the hand manipulation part 20. In addition, a liquid can also be transmitted into the guide wire lumen 4. A contrast medium can be supplied from the proximal end to the distal end of the core section 3, and the contrast medium can be ejected from the distal end of the core section 3 through the guide wire lumen 4. The proximal end of the core section 3 is fixed to a guide manipulation part 21 of the hand manipulation part 20. A radiopaque marker 5 is provided in the vicinity of the distal end of the core section 3. A position of the distal end of the core section 3 in an X-ray image can be detected by the radiopaque marker 5. A material of the core section 3 is preferably a material having flexibility such as a resin, an elastomer, or the like.

The outer layer section 6 is connected to the core section 3 at a position spaced a predetermined distance from the distal end of the guide catheter 2 toward the proximal side. The outer layer section 6 is a flexible cylindrical member extending from the connecting position with respect to the core section 3 to the proximal side. A distal end (a stopper) 6a of the outer layer section 6 is smoothly (with no step difference) connected to an outer surface of the core section 3. In the vicinity of the distal end 6a of the outer layer section 6, the outer surface of the outer layer section 6 is formed in a tapered shape having a diameter that gradually increases from the distal end 6a toward the proximal end of the outer layer section 6. In the portion formed in the tapered shape of the outer layer section 6, an inner diameter of the outer layer section 6 gradually increases from the distal end toward the proximal end of the outer layer section 6. A space in which the stent protection section 8 can be disposed is provided between the inner surface of the outer layer section 6 and the core section 3. The stent protection section 8 is disposed between the inner surface of the outer layer section 6 and the core section 3 such that the outer surface of the stent protection section 8 comes in contact with the inner surface of the outer layer section 6. The stent protection section 8 may be disposed between the inner surface of the outer layer section 6 and the core section 3 such that a clearance is provided between the outer surface of the stent protection section 8 and the inner surface of the outer layer section 6.

In order for the lumen of the tube stent 100 not to be crushed, the outer surface of the stent protection section 8 preferably comes in contact with the inner surface of the outer layer section 6. A position in a cross-sectional direction of the stent protection section 8 is set such that the stent protection section 8 slides with respect to the inner surface of the outer layer section 6 in a region from the distal end 6a of the outer layer section 6 to a protrusion 7 (to be described below) when the guide catheter 2 is deformed in a curved shape. At a position closer to a proximal side than a position at which the space between the inner surface of the outer layer section 6 and the core section 3 reaches a size in which the stent protection section 8 can be disposed, the inner diameter and the outer diameter of the outer layer section 6 are equal to each other.

As the distal end 6a of the outer layer section 6 is fixed to the core section 3, the stent protection section 8 disposed between the outer layer section 6 and the core section 3 cannot move to a distal side far from the distal end 6a of the outer layer section 6. That is, the portion in which the outer layer section 6 is fixed to the core section 3 functions as a stopper configured to restrict large movement of the stent protection section 8 to the distal side.

In the embodiment, the distal end 6a of the outer layer section 6 is fixed to the outer surface of the core section 3 by a known means such as thermal welding, adhesion, ultrasonic welding, caulking, or the like. The outer layer section 6 may be integrally formed with the core section 3.

The outer surface of the outer layer section 6 may be formed of an appropriately selected material and may undergo surface treatment such that frictional resistance with respect to the inner surface of the pusher catheter 10 is reduced.

A protrusion (a stopper) 7 protruding from the inner surface of the outer layer section 6 toward the space between the outer layer section 6 and the core section 3 is formed at the inner surface of the outer layer section 6. The protrusion 7 is formed by plastically deforming the outer layer section 6 inward from the outer surface side and raising the inner surface of the outer layer section 6. The protrusion 7 functions as a stopper to restrict large movement of the stent protection section 8 to the proximal side.

A length from the distal end 6a of the outer layer section 6 to the protrusion 7 when measured along the longitudinal axis O1 of the guide catheter 2 is larger than a dimension (the entire length) in an axial direction of the stent protection section 8. Specifically, the length from the distal end 6a of the outer layer section 6 to the protrusion 7 when measured along the longitudinal axis O1 of the guide catheter 2 is set depending on a relation with the dimension in the axial direction of the stent protection section 8 such that, when the region from the distal end 6a of the outer layer section 6 to the protrusion 7 receives an external force during use of the stent indwelling device 1 and is maximally deformed in a curved shape, the clearance is provided at least one of between the distal end of the stent protection section 8 and a distal end inside portion 6a1 of the outer layer section 6 and between the proximal end of the stent protection section 8 and the protrusion 7.

The proximal end of the outer layer section 6 is fixed to the guide manipulation part 21 of the hand manipulation part 20.

The stent protection section 8 is a substantially cylindrical member disposed between the core section 3 and the outer layer section 6. As shown in FIG. 2, in the embodiment, the stent protection section 8 is a coil body constituted by an element wire 9 wound in a spiral shape. The element wire 9 of the coil body constituting the stent protection section 8 has a substantially rectangular cross-sectional shape in a cross-section perpendicular to a centerline of the element wire 9. That is, in the embodiment, the coil body constituting the stent protection section 8 is a flat coil. The element wire 9 of the stent protection section 8 is tightly wound such that the element wire 9 comes in contact with itself in a state in which no external force is applied. A material of the element wire 9 of the stent protection section 8 may be a metal, or a resin having high hardness.

When the coil body constituting the stent protection section 8 is a flat coil, the stent protection section 8 has good stiffness with respect to compression in a centerline direction of the coil body, and does not easily buckle. Further, a shape of the element wire 9 constituting the coil body is not particularly limited, and the coil body may be formed by an element wire having a circular cross-section.

A pitch of the element wire 9 in the coil body constituting the stent protection section 8 is preferably less than 0.35 mm. When the pitch of the element wire 9 in the coil body constituting the stent protection section 8 is less than 0.35 mm, an effect of preventing plastic deformation of the tube stent 100 is high.

As shown in FIG. 1, the pusher catheter 10 is a flexible cylindrical member having a lumen 11 through which the guide catheter 2 passes. A relatively flexible soft section 12 in comparison with a proximal end section of the pusher catheter 10 is provided in the vicinity of the distal end of the pusher catheter 10. As the flexibility is maintained at the distal end section of the pusher catheter 10, insertion of the tube stent 100 is improved. A pusher manipulation part 25 of the hand manipulation part 20 is fixed to the proximal end of the pusher catheter 10. A position of the distal end of the pusher catheter 10 is closer to the distal end side than the protrusion 7 formed at the guide catheter 2 when a fitting concave section 24 and a fitting convex section 27, which will be described below, are fitted to each other to be in a fitted state.

As shown in FIG. 1, the hand manipulation part 20 has the guide manipulation part 21 and the pusher manipulation part 25. The guide manipulation part 21 is fixed to the proximal end of the guide catheter 2. The pusher manipulation part 25 is fixed to the proximal end of the pusher catheter 10.

The guide manipulation part 21 has a passage 22, a port 23, and the fitting concave section 24. The passage 22 comes in communication with the guide wire lumen 4 of the core section 3. The port 23 is used when a guide wire (not shown) is inserted through the passage 22 or when the passage 22 is connected to a liquid sending device (not shown). The fitting concave section 24 connects the guide manipulation part 21 and the pusher manipulation part 25.

The pusher manipulation part 25 is a cylindrical member having a passage 26 through which the guide catheter 2 is inserted so as to advance and retract. The fitting convex section 27 inserted into the fitting concave section 24 of the guide manipulation part 21 is formed at the proximal end of the pusher manipulation part 25.

When the fitting concave section 24 of the guide manipulation part 21 and the fitting convex section 27 of the pusher manipulation part 25 are fitted to each other to be in the fitted state, the guide catheter 2 and the pusher catheter 10 can be integrally operated in a direction along the longitudinal axis O1. When the fitted state of the fitting concave section 24 and the fitting convex section 27 is released, the guide catheter 2 can be extracted to the proximal end side with respect to the pusher catheter 10.

Figure 3:
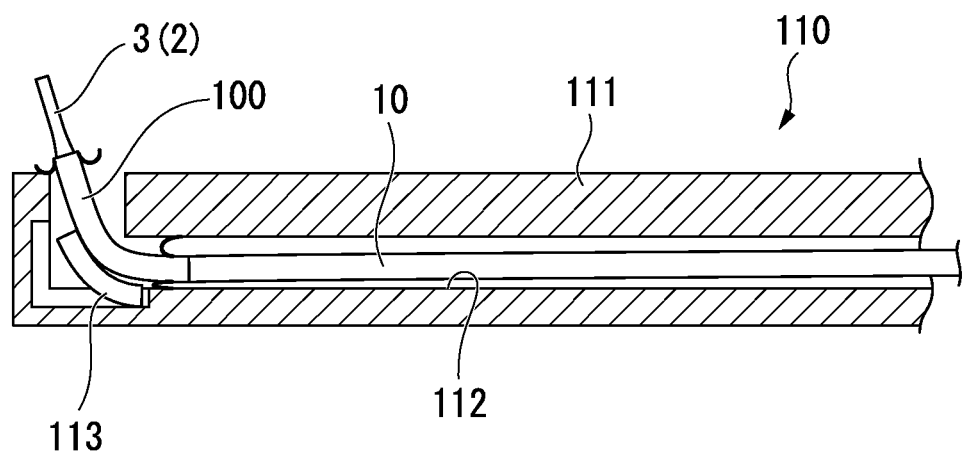
FIG. 3 is a view for describing a process in use of the stent indwelling device.
Figure 4:
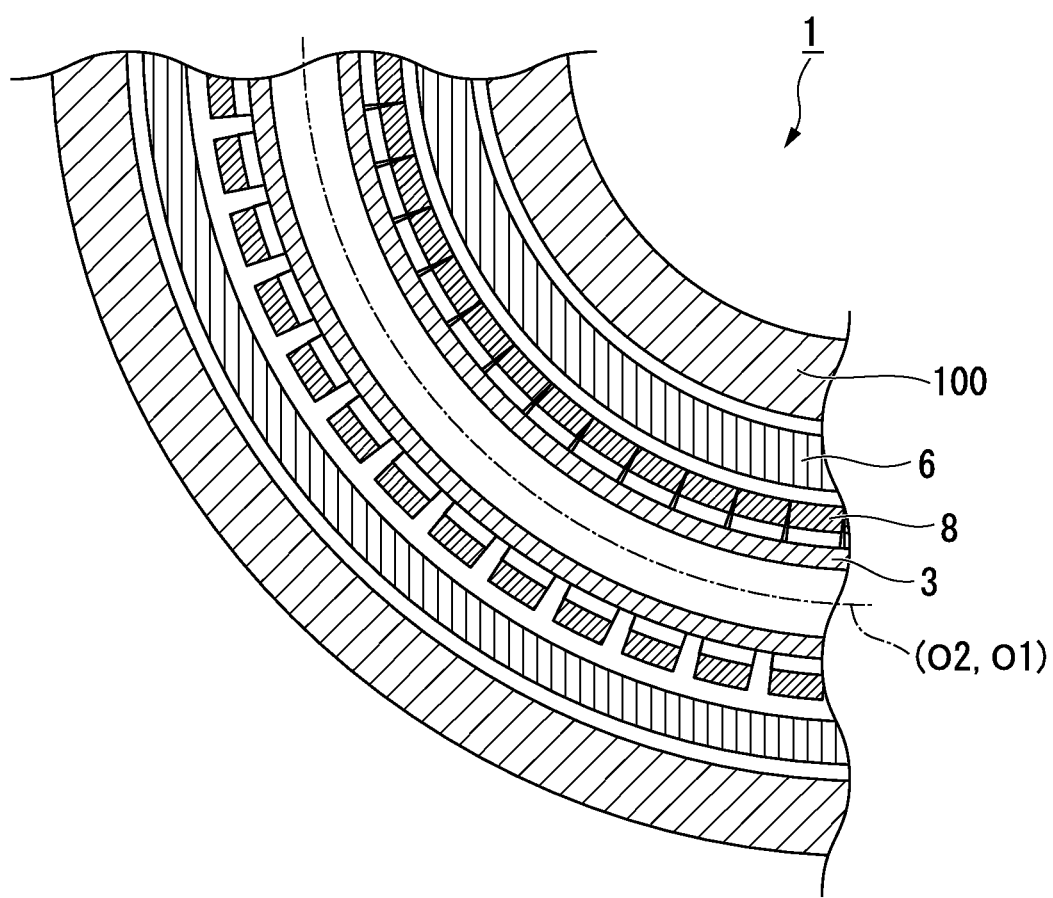
FIG. 4 is a view for describing an action of the stent indwelling device.

Next, an action of the stent indwelling device 1 according to the embodiment will be described. FIG. 3 is a view for describing a process in use of the stent indwelling device. FIG. 4 is a view for describing an action of the stent indwelling device.

When a procedure of guiding the tube stent 100 to an indwelling target area is performed using the stent indwelling device 1, in the state shown in FIG. 1, the stent indwelling device 1 is prepared. That is, the guide catheter 2 is inserted into the pusher catheter 10. The fitting concave section 24 and the fitting convex section 27 are fitted to each other. At a farther distal side of the distal end of the pusher catheter 10, the distal end section of the guide catheter 2 is inserted into the tube stent 100. Here, the position of the distal end of the pusher catheter 10 is closer to the distal side than the protrusion 7 formed at the guide catheter 2. For this reason, the tube stent 100 is roughly positioned between the stopper of the distal side (the distal end 6a of the outer layer section 6) and the stopper of the proximal side (the protrusion 7) in the direction along the longitudinal axis O1 of the guide catheter 2.

When the tube stent 100 is guided to the indwelling target area using the stent indwelling device 1, for example, an endoscope 110, a portion of which is schematically shown in FIG. 3, is used together therewith. As an example, when the tube stent 100 is placed in the bile duct, the side view type endoscope 110 that can arrive at the duodenum through the digestive tract is used with the stent indwelling device 1. The side view type endoscope 110 has an insertion section 111 inserted into the digestive tract, and the insertion section 111 has a treatment tool channel 112 and a raising base 113. The guide catheter 2 and the pusher catheter 10 of the stent indwelling device 1 can be inserted into the treatment tool channel 112 together with the tube stent 100. The raising base 113 is mounted in the vicinity of the distal end of the treatment tool channel 112, and controls directions of the guide catheter 2 and the pusher catheter 10.

In the embodiment, the raising base 113 in the side view type endoscope 110 curves the guide catheter 2 about 90 degrees, and for example, directs the distal end of the guide catheter 2 to the duodenal papilla communicating with the bile duct. For this reason, the raising base 113 applies an external force to the guide catheter 2 to cause the guide catheter 2 to curve.

When the guide catheter 2 is deformed in a curved shape in the raising base 113, the core section 3 and the outer layer section 6 of the guide catheter 2 are flexibly deformed. The stent protection section 8 disposed between the core section 3 and the outer layer section 6 is curved in a state in which a cross-section perpendicular to a centerline O2 (see FIG. 4) of the coil body constituting the stent protection section 8 is held in a substantially circular shape. For this reason, the outer layer section 6 is supported by the stent protection section 8 such that the inner surface of the outer layer section 6 is curved while the cross-section perpendicular to the longitudinal axis O1 in the inner surface of the outer layer section 6 is maintained in a substantially circular shape.

As the inner surface of the outer layer section 6 is curved with being supported by the stent protection section 8, even in the outer surface of the outer layer section 6, the outer surface of the outer layer section 6 is curved while the cross-section perpendicular to the longitudinal axis O1 is maintained in a substantially circular shape. For this reason, even in the inner surface of the tube stent 100 which is deformed in a curve while in contact with the outer surface of the outer layer section 6, the inner surface of the tube stent 100 is curved while the cross-section perpendicular to the axial direction of the tube stent 100 is maintained in a substantially circular shape.

When the stent protection section 8 is not provided, if the core section 3 and the outer layer section 6 are bent with a large curvature, the core section 3 and the outer layer section 6 may be kinked. In this case, the guide catheter 2 may be deformed in a bent shape at the kinked portion, and the tube stent 100 may be bent. As the tube stent 100 is bent and kinked, a cross-sectional area of the space that becomes a flow path of a body fluid or the like in the lumen of the tube stent 100 is reduced, and a probability of the tube stent 100 closing is increased. In particular, when a structure that can be easily plastically deformed is included in the tube stent 100, for example, when the coil constituted by the metal wire is provided to maintain a shape of the tube stent 100, the cross-section of the lumen of the tube stent 100 may not return to the original circular shape even when the bent state of the tube stent 100 is released.

On the other hand, in the stent indwelling device 1 of the embodiment, the stent protection section 8 holds the inner surface of the tube stent 100 via the outer layer section 6 such that the tube stent 100 is not kinked. For this reason, the lumen of the flexible tube stent 100 is not crushed in the indwelling process of the tube stent 100.

When the guide catheter 2 is in the curved state, lengths measured parallel to the longitudinal axis O1 of the guide catheter 2 are different at the curved inner circumferential side and the outer circumferential side of the guide catheter 2. That is, the curved outer circumferential side of the guide catheter 2 is increased to be larger than the inner circumferential side. Here, in the stent protection section 8 constituted by the coil body of the tight winding, the dimension measured along the centerline of the stent protection section 8 is larger than the dimension in which the stent protection section 8 is in a linear state. In the embodiment, the stent protection section 8 is not fixed to the outer surface of the core section 3 and the inner surface of the outer layer section 6. For this reason, when the guide catheter 2 is curved as shown in FIG. 4, in the curved inner side of the stent protection section 8, as the adjacent end surfaces of the coil come in contact with each other with no clearance, the stent protection section 8 contracts in the axial direction. In the curved outer side of the stent protection section 8, as the clearance is generated between the adjacent end surfaces of the coil, the stent protection section 8 extends in the axial direction. Accordingly, when the stent protection section 8 of the guide catheter 2 is curved, the flexibility of the guide catheter 2 is not largely damaged. In addition, in the direction along the longitudinal axis O1 of the guide catheter 2, spaces that allow expansion of the stent protection section 8 are formed at both end sides of the stent protection section 8. For this reason, the external force of compressing the stent protection section 8 in the direction along the centerline to impede the stent protection section 8 from being curved is not applied to the stent protection section 8, and flexibility of the guide catheter 2 in the portion at which the stent protection section 8 is provided is not easily reduced.

In the embodiment, the stent protection section 8 is not fixed to the core section 3 and the outer layer section 6 at all. For this reason, when the stent protection section 8 expands, the stent protection section 8 can escape to either the distal end side or the proximal end side of the stent protection section 8 having a gap.

The distal end of the guide catheter 2 is appropriately directed toward the duodenal papilla, and the distal end of the guide catheter 2 is guided to the bile duct by a known means. A position of the distal end of the guide catheter 2 is easily recognized in an X-ray image using the radiopaque marker 5. Next, the fitted state of the fitting concave section 24 and the fitting convex section 27 in the hand manipulation part 20 is released, and the guide catheter 2 is extracted to the proximal end side. Accordingly, the guide catheter 2 is extracted from the tube stent 100 while the tube stent 100 is supported by the distal end of the pusher catheter 10. As a result, the tube stent 100 is placed in a state in which the distal end of the tube stent 100 is disposed in the bile duct, and the proximal end of the tube stent 100 is disposed in the duodenum.

In this way, the stent indwelling device 1 according to the embodiment has the stopper disposed to allow expansion of the stent protection section 8. For this reason, the flexibility of the guide catheter 2 is not easily reduced, and the guide catheter 2 can easily pass through the severely bent portion having a large curvature.

As described above, the stent indwelling device 1 according to the embodiment has an effect that the lumen of the flexible tube stent 100 is not crushed in the indwelling process of the tube stent 100 and an effect that the guide catheter 2 easily passes through the severely bent portion having a large curvature.

In the embodiment, the stent protection section 8 may be a roughly wound coil if the roughly wound coil has stiffness to support the tube stent 100 such that the lumen of the tube stent 100 is not crushed.

When the stent protection section 8 is the roughly wound coil, the dimension (the entire length) of the stent protection section 8 may not expand even when the stent protection section 8 is curved. In this case, the guide catheter 2 may be configured such that the stent protection sections 8 come in contact with the stopper of the distal side of the guide catheter 2 and the stopper of the proximal side of the guide catheter 2.

A part of the stent protection section 8 may be fixed to the core section 3 or the outer layer section 6.

Hereinabove, while the exemplary embodiment of the present invention has been described, the present invention is not limited to the embodiment. Additions, omissions, substitutions, and other modifications of the configurations may be made without departing from the spirit and scope of the present invention. The present invention is not limited to the above description but will be limited only by the scope of the accompanying claims.

What is claimed is:

1. A stent indwelling device configured to place a tube stent in a lumen tissue, the stent indwelling device comprising:
  a guide catheter having a longitudinal axis and configured to be inserted into the tube stent from a distal end side of the guide catheter; and
  a pusher catheter having a lumen into which the guide catheter is inserted, wherein
  the guide catheter includes:
    a core section having flexibility, the core section being longer than a dimension in an axial direction of the tube stent;
    an outer layer section having a tube shape surrounding an outer circumference of the core section, the outer layer section being fixed to the core section to define a cavity;
    a stent protection section movably disposed in the cavity between the core section and the outer layer section, a distal end and a proximal end of the stent protection section being positioned such that the stent protection section has a length longer than the dimension in the axial direction of the tube stent, the stent protection section being formed in an annular shape about the longitudinal axis when seen from a direction along the longitudinal axis, having stiffness resisting compression inward in a radial direction perpendicular to the longitudinal axis, and having flexibility in a direction in which the guide catheter is curved; and
    distal and proximal stoppers being spaced in the direction along the longitudinal axis at distal and proximal ends of the cavity to allow a predetermined range of expansion of the stent protection section in the direction along the longitudinal axis and to restrict movement of the stent protection section in the direction along the longitudinal axis outside of the predetermined range.

2. The stent indwelling device according to claim 1, wherein
   the core section and the outer layer section are fixed to each other at a distal end of the outer layer section, and
   a distal end side of the outer layer section is formed to have a diameter gradually reduced from a proximal end side of the guide catheter toward the distal end side of the guide catheter, and smoothly connected to an outer surface of the core section.

3. The stent indwelling device according to claim 1, wherein
   the proximal stopper is a protrusion formed on the outer layer section and protruding into the cavity between the core section and the outer layer section, and
   the protrusion is configured to restrict the movement of the stent protection section in the direction along the longitudinal axis by coming in contact with the stent protection section.

4. The stent indwelling device according to claim 1, wherein the stent protection section is constituted by an element wire having a spiral structure of tight winding.

5. The stent indwelling device according to claim 1, wherein
   the outer layer section is formed in a cylindrical shape having a circular cross-section,
   the stent protection section is formed in a substantially cylindrical shape having a circular cross-section, and
   a difference between an inner diameter of the outer layer section and an outer diameter of the stent protection section is equal to or less than 0.5 mm.

* * * * *